July 27, 1948. L. S. HOPKINS Plant Pat. 804
PEONY VARIETY
Filed Sept. 11, 1944
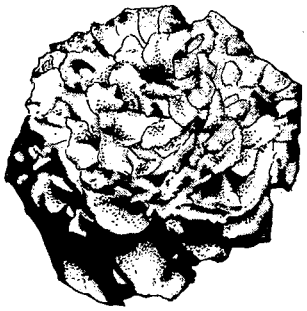
Inventor
L. S. Hopkins
By Paterson, Wright & Parsons
Attorneys Patented July 27, 1948

Plant Pat. 804

UNITED STATES PATENT OFFICE

804

PEONY VARIETY

Lewis S. Hopkins, Canton, Mo.

Application September 11, 1944, Serial No. 554,062

1 Claim. (Cl. 47—60)

The present invention relates to improvements in peony varieties the original having been grown from seed. Reproduction can be obtained only by root and crown division.

Among the outstanding features of this new variety are its fully and uniformly double flowers and the excellent keeping qualities thereof, together with their extremely strong delicate rose fragrance and the fastness of their color which will not fade or bleach in the sun.

The fragrance, its keeping qualities as a cut flower, its quality of non-fading or bleaching distinguish this peony variety from other peonies.

The accompanying illustration which is a part of this specification shows the new peony variety.

*The Plant*

Growth habit: Has strong numerous roots which are fleshy and fascicled.

Blooming habit: Is late blooming.

Stems: There are several stems, depending on age of plant, which are rigidly erect and glabrous. The stems are ½ to ¾ inches in diameter at their base and reach a height of 24 to 30 inches. The stems are sufficiently stout and strong to hold flowers rigidly erect at all times.

Foliage: Abundant, running from 7 to 12 leaves; the leaves are ternately decompound green above, lighter beneath, long petioled; petiole deeply channeled or grooved; groove red, rest of petiole green; segments one-half–two inches wide; two–four inches long; apex acute; margin entire; lanceolate; each leaflet conspicuously bordered with a narrow line of red which is especially prominent in young leaves; glaborous; petioles three–six inches long.

*The flower*

Blossom:

*Form.*—Fully and uniformly double. No carpels, stamens, or staminodia have ever been produced.

*Size.*—Averages 7 inches in diameter but frequently reached 8½ inches and averages 5 inches in depth and frequently reached 5½ inches.

*Color.*—An uniform light rose pink which will not fade or bleach in the sun.

*Fragrance.*—Unusually sweet scented, having a delicate rose fragrance. A single flower will scent an entire room.

*Keeping quality.*—Excellent. Very long lasting as a cut flower.

Having thus disclosed my invention I claim:

A variety of peony plant substantially as herein disclosed, characterized by its strong sweet rose scented fragrance and exceptional keeping qualities as a cut flower and the non-fading quality of its double blossom.

LEWIS S. HOPKINS.

REFERENCES CITED

The following references are of record in the file of this patent:

UNITED STATES PATENTS

| Number | Name | Date |
|---|---|---|
| Pl. Pt. 612 | Engle | Jan. 4, 1944 |